(12) United States Patent
Haines

(10) Patent No.: US 6,196,055 B1
(45) Date of Patent: Mar. 6, 2001

(54) PAINT AND SURFACE COATING AIR PERMEABILITY DEMONSTRATION AND TESTING APPARATUS

(75) Inventor: Stuart Haines, Los Angeles, CA (US)

(73) Assignee: Textured Coatings of America, Inc., Panama City, FL (US)

(*) Notice: Subject to any disclaimer, the term of this patent is extended or adjusted under 35 U.S.C. 154(b) by 0 days.

(21) Appl. No.: 09/250,622

(22) Filed: Feb. 16, 1999

(51) Int. Cl.[7] .................................................. G01N 15/08
(52) U.S. Cl. ............................................................ 73/38
(58) Field of Search ................................................. 73/38

Primary Examiner—Hezron Williams
Assistant Examiner—Jay L. Politzer
(74) Attorney, Agent, or Firm—Baker & McKenzie

(57) ABSTRACT

A method and apparatus for testing the vapor or gas permeability of a paint, sealant, textured coating or other surface coating. A test block is provided having a porous substrate coated with the test coating. The test block is mounted in a bubble testing apparatus between a pressure chamber and a liquid vessel. Water is provided in the liquid chamber and air is pumped into the pressure chamber. As the pressure of the pressure chamber rises above that of the liquid chamber, a pressure gradient is created. Bubbles can be visually observed in the water filling the liquid chamber if the test coating is vapor or gas permeable.

16 Claims, 3 Drawing Sheets

US 6,196,055 B1

PAINT AND SURFACE COATING AIR PERMEABILITY DEMONSTRATION AND TESTING APPARATUS

FIELD OF THE INVENTION

The present invention relates to an apparatus and method for demonstrating the vapor permeability of paint or other types of surface coatings.

BACKGROUND OF THE INVENTION

Exterior and interior wall structures commonly are coated with a surface coating such as paint, sealer, textured coatings, stucco and so on. These surface coatings have various characteristics, including color, texture, moisture permeability and vapor permeability. It is desirable to have a surface coating that acts as a moisture barrier, but also allows the coated surface to breathe. This is because if the coating acts as a vapor barrier, this can lead to moisture build up, spotting, chipping, cracking, peeling, of the surface coating. Likewise, mildew can build up in the coated surface, and biological growth can occur, such as the growth of algae.

Resistance to moisture penetration, combined with vapor or gas permeability, is commonly viewed to be favorable characteristics of surface coatings. Accordingly there is a need to demonstrate or test these characteristics. For example, there is a need to demonstrate these characteristics to purchasers, users or consumers of surface coatings.

One apparatus for measuring vapor transmission rates is used in testing laboratories. Such an apparatus may use a cup or other enclosure with a permeable surface across an opening. The surface may be coated with the substance to be tested. Likewise a desiccant is placed inside the cup to absorb vapor. The cup is then placed in an environment with a known humidity level. As the desiccant in the interior of the cup absorbs moisture transmitted through the coated barrier, the cup can be weighed to determine the weight increase and therefore the vapor transmission rate.

This known apparatus suffers from various deficiencies for use as a demonstration or testing device. For example, it takes a relatively long period of time for moisture to transfer through the vapor barrier. Likewise, a measuring apparatus is required in order to determine the increase in weight of the cup as the desiccant absorbs moisture. Moreover, the transmission of the vapor or gas cannot easily be seen visually, or the liquid permeability is not readily observed. Without such visual demonstrability, the use of the known apparatus as a demonstration tool is somewhat limited.

Accordingly, there is a need for a demonstration and testing apparatus illustrating permeability characteristics of a surface coating.

SUMMARY OF THE INVENTION

The present invention alleviates to a great extent the disadvantages of the known apparatus and methods for demonstrating and testing the permeability of surface coatings by providing an apparatus that provides observable visual data, such as bubbles rising through water, as vapor or gas passes through the surface coating being demonstrated or tested.

In a preferred embodiment the apparatus of the present invention includes a pressurized gas or vapor supply providing the pressurized gas or vapor to a pressure chamber. On a side of the pressure chamber is a test block made of a relatively porous material. The test block is coated with the surface coating to be demonstrated, on at least a portion of its surface (and corresponding interstices). In one embodiment the test block is coated on all surfaces with a sealant, paint, textured coating, or other material to be tested. Alternatively a second coating may also be used. For example, the test block may be coated with a sealant and a textured exterior coating, similar to the way such products might be used on the outer walls of a building.

The block with the test coating is in communication with the interior of the pressure chamber, as well as unpressurized exterior. Preferably the test block is mounted in the top side of the pressure chamber and a liquid vessel is above the test block. In operation, the liquid vessel is filled with water or another suitable fluid. The portion of the test block exposed to the liquid vessel is in contact with the fluid. Before the pressure chamber, opposite the test block from the liquid vessel, is pressurized, if the coating of the test block is fluid resistant, then water is not observed seeping through to the pressure chamber (which may be unpressurized). Then, when the pressure chamber is pressurized, a pressure gradient is created, going from the pressurized pressure chamber, through the block, to the liquid vessel. When the pressure gradient is created, if the coating of the test block is vapor permeable, then vapor (or gas) can be observed as bubbles passing through the fluid, emanating from the test block. This is because a pressure gradient is created between the pressure chamber and the outside atmosphere through the test block.

In the preferred embodiment, the gas or vapor supply is in the form of a rubber ball that can be manually pumped in order to pressurize the interior of the pressure chamber to a higher pressure than the surrounding atmosphere. The liquid vessel is filled with water and then bubbles can be observed rising through the water, from the test block. This demonstrates the vapor permeability of the test block, and any surface coating applied to it.

These and other features and advantages of the present invention will be appreciated from review of the following detailed description of the invention, along with the accompanying figures in which like reference numerals refer to like parts throughout.

DETAILED DESCRIPTION OF THE INVENTION

Figure 1:
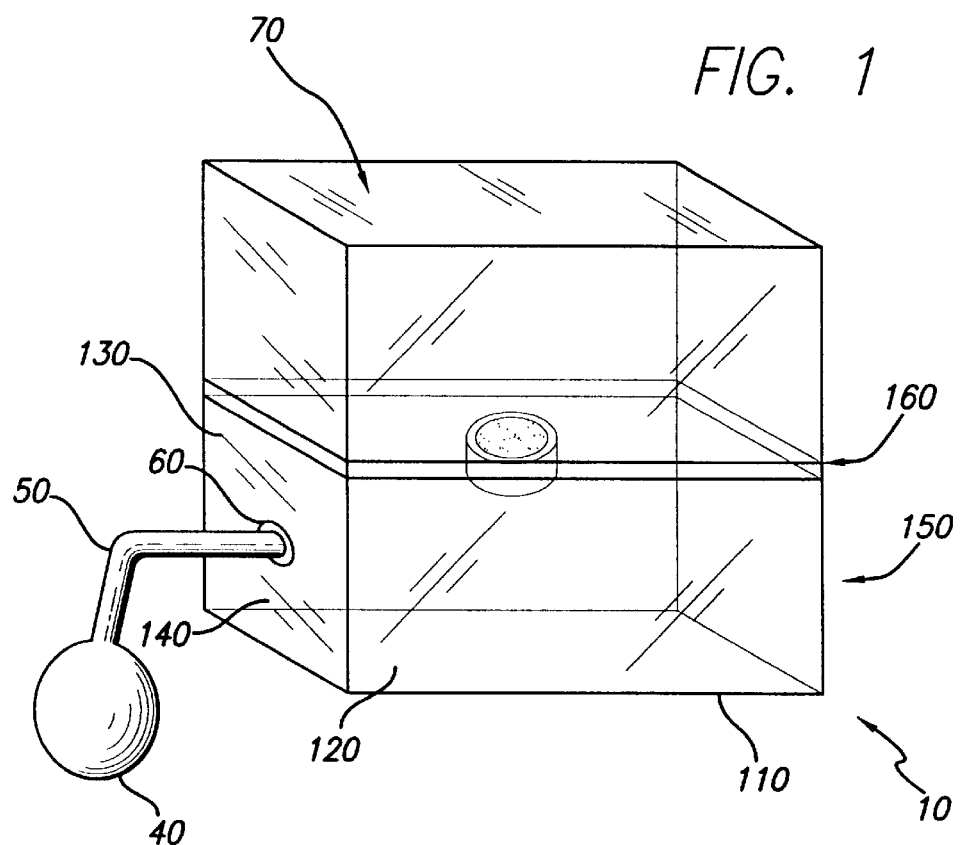
FIG. 1 is a perspective view of an embodiment of an apparatus in accordance with the present invention.

In accordance with the present invention, a system is provided for demonstrating or testing the gas or vapor permeability of immaterial, such as a surface coated with a paint, sealer, textured coating or any other form of surface coating. As illustrated in the figures, a demonstration apparatus 10 is provided, which includes a pressure chamber 20, a test block 30, a gas source 40, optional gas line 50, plug or valve 60 into the interior of the pressure chamber 20 and liquid vessel 70. The pressure chamber 20 can be of any size or shape, as long as it can provide a pressure gradient across the test block 30 to the fluid chamber 70. In an alternative embodiment, the pressure chamber is omitted, but rather the pressure source 40 interacts directly with the test block 30 providing a pressure gradient across test block 30 to the fluid chamber 70. In either case, the demonstration apparatus 10 provides an area in proximity to the test block 30 in which a pressure gradient can be created.

Figure 2:
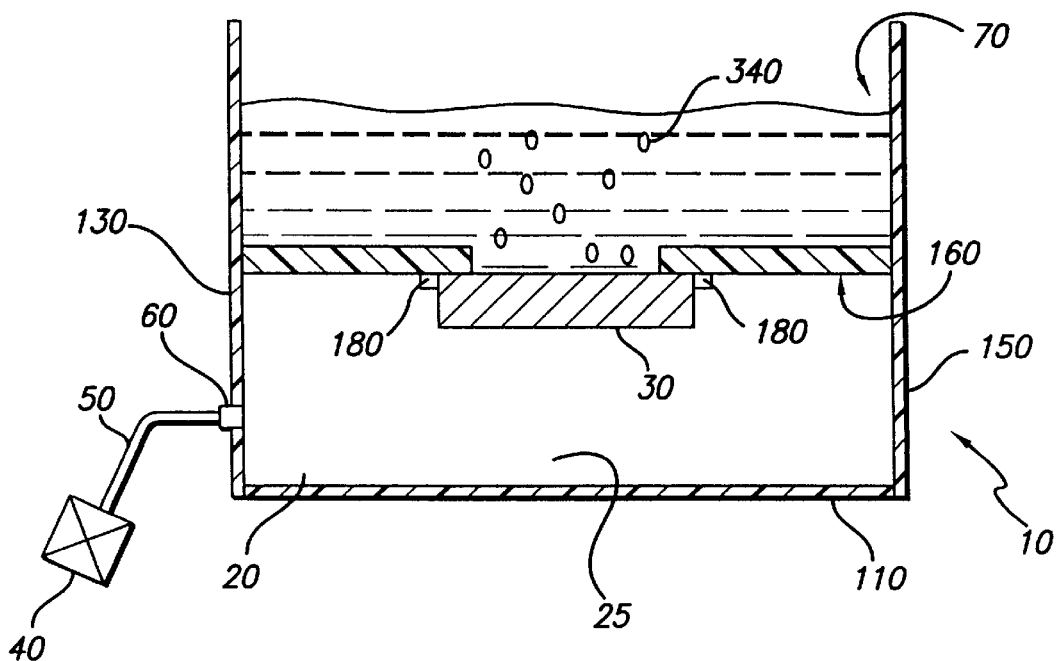
FIG. 2 is an elevational view of an apparatus in accordance with the present invention.
Figure 3:
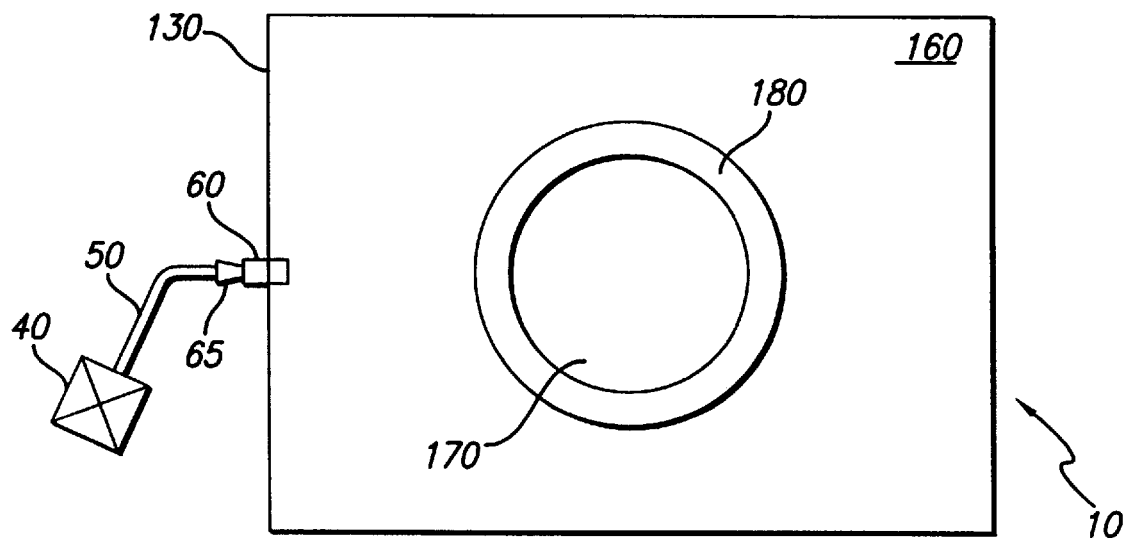
FIG. 3 is a top view of an apparatus in accordance with the present invention.

Preferably, both the pressure chamber 20 and the fluid chamber 70 are clear so that their respective interiors can readily be viewed. Accordingly, in the preferred embodiment suitable materials for both the liquid vessel 70 and pressure chamber 20 are clear materials such as glass, and various types of plastic such as plexiglass. To provide increased resistance to breaking, as well as increased durability it is preferred that the materials be selected to be relatively resistant to impacts, such as plastics. Alternatively, the pressure c chamber 20 and/or fluid chamber 70 are entirely, or partially opaque. In this alternative embodiment a clear portion or window can be provided as desired. Alternatively, as depicted in FIGS. 1–3, the top of the fluid chamber 70 can be open to the exterior, allowing visual observation from above.

In the preferred embodiment, a pressure chamber 20 is provided. A gas source 40 is in communication with the interior of the pressure chamber 25 via a gas line 50 and through entry port 60 into the interior 25 of the pressure chamber. In this way gas at a pressure higher than the ambient pressure can be provided from the gas source 40 to the pressure chamber 20. Any gas source, such as a gas tank or manual pump can be used. Likewise any gas, such as oxygen, nitrogen, carbon dioxide, helium, hydrogen, or preferably, ambient air can be used. In the preferred embodiment, the gas source 40 is a rubber squeeze ball, such as is widely known, providing a one-way valved intake port for intaking ambient air into the interior of the rubber ball. This embodiment is illustrated in FIG. 1, where the squeeze ball is labeled as element 40. As the squeeze ball is compressed (such as by manual squeezing), pressurized air goes through the gas line 50 to the interior of the pressure chamber 20. The gas line 50 also can be made of any material that can transmit the pressurized gas, but preferably has flexibility in order to provide a range of motion for the user. In the preferred embodiment the gas line 50 is a rubber hose, but it also can be made of plastic or any materials suitable for transferring pressurized gas from the gas source 40 to the interior 25 of the pressure chamber 20.

The intake port 60 can be either a passive or valved port. For example, in one embodiment, the port 60 can receives the gas line 50 and provide a conduit into the interior of the chamber 20. In an alternative embodiment, the port 60 includes a one-way valve allowing gas to flow from the hose 50 or the gas supply 40 to the interior 25 of the pressure chamber 20. In another embodiment, the gas line 50 is coupled to a coupling unit 65 that fits with the port 60. The coupling unit 65 can be passive in that it only includes the proper shape for being received by the port 60. Alternatively it can include a valve for providing one-way gas flow from the gas supply 40 and gas line 50 through the unit 65 and port 60 into the interior 25 of the pressure chamber 20.

As noted above the pressure chamber 20 can be of any shape. In the illustrated embodiment a generally rectangular cubic shape is provided, however rounded or irregular walls also can be used. The preferred embodiment will be described here. The pressure chamber 20 in the cubic embodiment, has six walls, a bottom 110, four sides 120, 130, 140, 150 and top 160. In the illustrated embodiment the port 60 is in sidewall 130, although it should be understood that the port can be placed in any wall of the pressure chamber 20 providing access to the exterior. Likewise, the test block 30 is illustrated as being placed in the top wall 160 of the pressure chamber 20. However, the test block 30 can be placed in any wall, that provides access to the liquid vessel 70. Preferably this is the top wall 160 so that gravitational force acts to retain fluid within the liquid vessel 70 and against the test block 30.

The test block 30 is mounted on the top wall 160 of the pressure chamber 20, as illustrated in the figures. Preferably a gas-tight seal is provided between the test block 30 and the wall 160 so as to inhibit any leakage during use. In the illustrated embodiment an overlap exists between the wall and the test block in which a sealing material 180 is placed. In other words an aperture 170 is provided in the top wall 160 although the aperture is of a smaller dimension than the test block, providing the overlap. In addition a caulking material 180 is preferably used to provide the seal between the test block and the top wall 160, although any type of sealing material arrangement can be used. It should also be noted that in the preferred embodiment, the top wall 160 also constitutes a bottom surface of the liquid vessel 70, although separate walls could also be used.

The uncoated portion of the test block 30 will be referred to as the test block substrate 210, as discussed further below. The test block substrate 210 can be made of any material that provides some through-flow of gas or vapor. In the preferred embodiment a porous stone is used, such as pumice stone, or porous sandstone. Alternatively any other porous material can be used such as a porous ceramic, cellulosic or polymeric material. Because it is preferred that a visual demonstration be provided, it is also preferred that the test block substrate 210 be sufficiently porous to provide a sufficient rate of gas flow to be visually observed as bubbles passing through a fluid. However, other, less porous materials also can be used if observation is aided by magnifying instruments or gas detectors. In such a case the test block substrate 210 can also be constructed of wood or other porous materials. In a preferred embodiment the test block substrate 210 is permeable to liquids, such as water, in addition to being gas or vapor permeable.

Figure 4:
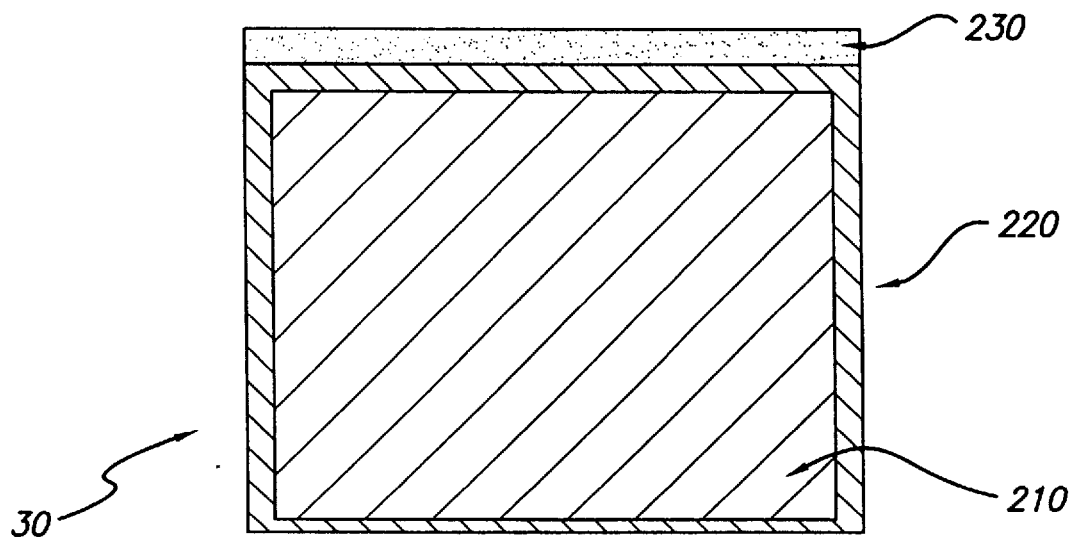
FIG. 4 is a cross-sectional view of an embodiment of a test block in accordance with the present invention.
Figure 5:
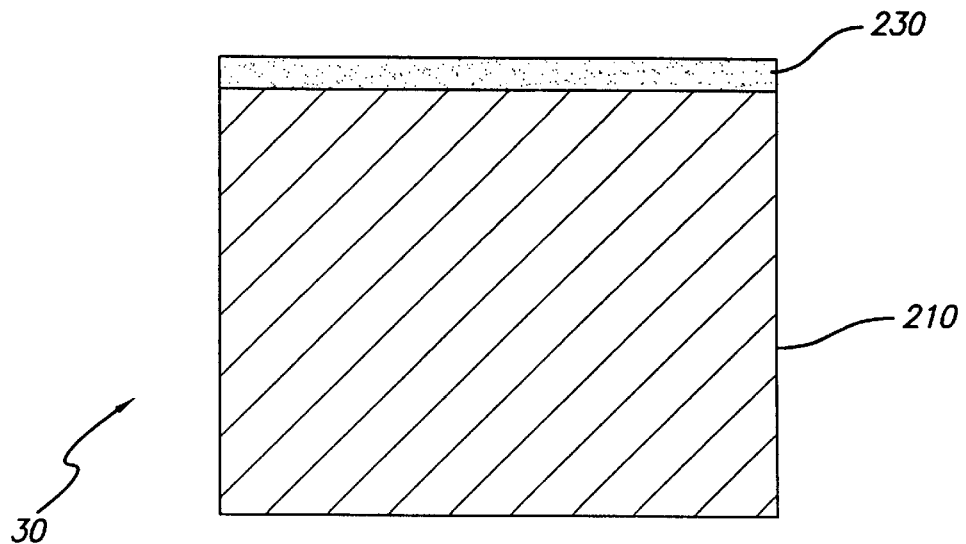
FIG. 5 is a cross-sectional view of another embodiment of a test block in accordance with the present invention.

In use, it is desired to demonstrate the permeability characteristics of a surface coating. Accordingly, the test block 30 preferably is treated with such a surface coating. In one embodiment, the test block substrate material 210 is coated with a sealant, in addition to a paint, textured coating, stucco or other coating material. Alternatively, the substrate material 210 can be coated only with one form of coating material, such as a sealant, paint, textured coating, stucco or other coating material Two exemplary embodiments of the test block 30 are illustrated in FIGS. 4 and 5. A two-coating embodiment is illustrated in FIG. 4 and a single coating embodiment is illustrated in FIG. 5. It should be understood that any number of coatings can be used as well. The test block 30 includes the substrate or base material 210. This is the porous material already described above. A coating 220 can be placed on the test block by any means, such as using a paint brush or immersion. In the illustrated embodiment, the coating 220 is placed on the porous material 210 by immersion, and thereby covers all the surfaces of the test block. In a preferred embodiment, this coating 220 can be a sealer. One suitable sealer is a clear sealer or sealant known as the RAINSTOPPER® 140™, which is available from Textured Coatings of America, 2422 East 15th Street, Panama City, Fla. This sealer is known as providing a fluid barrier, but still allows the underlying coated surface to "breath," in other words to allow vapor permeability. A second coating may also be provided, such as a textured coating, paint or other form of wall or surface coating. One suitable coating is TEX-COTE®, also available from Textured Coatings of America.

In an alternative embodiment, as illustrated in FIG. 5 the porous material 210 has one surface coated by a surface coating 230. Again, any coating material can be used. It should also be noted that the sealant, discussed above, can be coated on a single surface as well as multiple surfaces as illustrated in FIG. 4. Likewise the material 230 can be coated on multiple surfaces.

A portion of the test block 30 preferably is in communication with the interior of liquid vessel 70. The liquid vessel 70 can be made of any material, as long as it is substantially impermeable to liquids. One wall of the liquid vessel 70 includes an aperture providing communication with the test block 30 in the preferred embodiment. In the illustrated embodiment, the bottom wall of the fluid vessel 70 includes the aperture, as described above. It should be noted that alternate embodiments do not have the test block 30 in direct contact with the water. For example, the test block may be distant from the liquid vessel 70, but in communication with it, such as through a hose with a valve.

Figure 6:
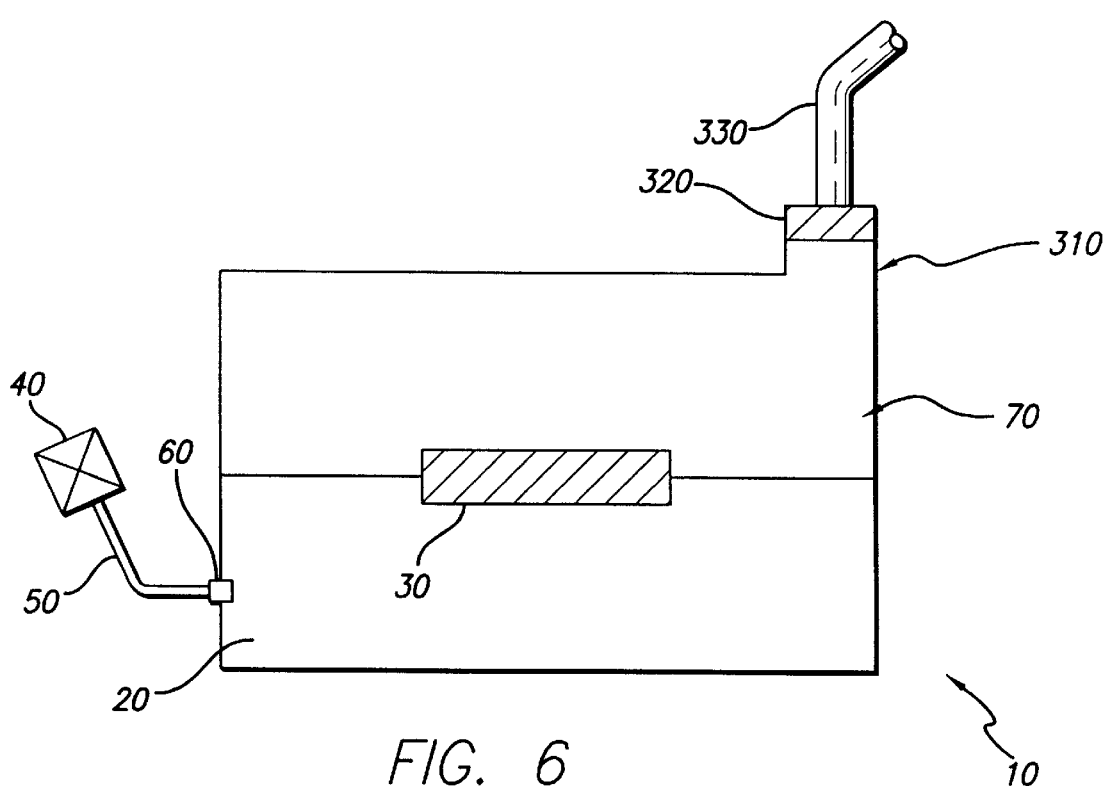
FIG. 6 is a cross-sectional view of an alternate embodiment of an apparatus in accordance with the present invention.

The liquid vessel 70 also includes an intake portion allowing for fluid to be input into the vessel 70. In the preferred embodiment the intake portion is an open topside of the fluid vessel 70, as illustrated in FIGS. 1 and 2. However, an alternate intake portions 310 also may be used. For example, a closable aperture may be provided, as illustrated in FIG. 6. In this alternative embodiment, the intake aperture can be sealed, such as using a cap 320 if desired. Alternatively, the cap intake portion 310 can include an outlet line 330 that can goes to a gathering or measuring apparatus to measure the amount of gas passing from the pressure chamber 20 to the liquid chamber 70. In yet another embodiment, the liquid chamber 70 can be filled with ambient air. In this case, there would be no visual display of the transmission through the test block 30. However, the line 330 can be used to measure properties of the gas in the chamber 70 and thereby determine the flow through the test block 30. For example, the pressure inside chamber 70 can be measured. Alternatively, the volume of gas flow through the test block 30 can be measured.

In assembly, the test block 30 is prepared for example by being dipped in a sealing material to 20 and then subsequently coated with a textured coating 230, as already discussed above and illustrated in FIG. 4. Once the test block 30 is prepared the apparatus can be assembled. The test block 30 is affixed to one wall of the pressure chamber 20 in a sealed fashion, such as using caulk 180.

In operation of the preferred embodiment, as illustrated in FIGS. 1–3, water (or other liquid) is placed in fluid chamber 70. The apparatus 10 is retained in a generally upright position allowing the liquid to settle on the bottom of the liquid vessel 70 and in communication with a surface of the prepared test block 30. If the coating on the test block is impervious to liquid, no liquid will be observed passing from the liquid vessel 70 through the test block 30 and into the pressure chamber 20. It should be noted that at this stage in operation, the pressure chamber 20 is not yet pressurized. Accordingly, the pressure gradient is running from the liquid vessel 70 across the test block 30 and into the interior space 25 of the test chamber 20. In order to further illustrate the impermeability to water characteristics of the coated test block 30, the test chamber 20 can also be evacuated. In this demonstration, instead of a pressure source 40 being provided a vacuum source is provided, in the same way as illustrated with element 40 in the figures. If the test block is impermeable to fluids, such as water, even under these vacuum conditions, it may be demonstrated that fluid does not pass through the test block 30.

The air (or more generally gas) permeability characteristics of the coated test block 30 are preferably demonstrated by keeping the liquid chamber 70 still filled with liquid (such as preferably water), but then pressurizing the pressure chamber 20. This is done, for example by squeezing the rubber ball (preferred embodiment of pressure source 40) to force air through line 50 and through port 60 (and optionally connector 65) into the interior 25 of pressure chamber 20. By so forcing air into the interior 25 of pressure chamber 20, the pressure in chamber 20 is elevated. Once the pressure inside pressure chamber 20 exceeds the ambient pressure, including the weight pressure of the liquid in liquid vessel 70, a pressure flow gradient from the interior 25 of pressure chamber 20 across test block 30 and into liquid chamber 70 is provided. With this pressure gradient, if the material coating test block 30 is permeable to gas (i.e. air) then the pressure gradient will cause gas to pass through test block 30 into pressure chamber 70. This can be visually observed as bubbles 340 coming from the test block 30 and passing through the liquid filling liquid vessel 70. The bubbles 340 are a visual demonstration of the flow of gas through the test block 30.

It should be noted that if a sufficiently porous material 210 for test block 30 is used, it will allow liquid to pass from liquid vessel 70 into pressure chamber 20, when pressure chamber 20 is not yet pressurized. This can provide a visual demonstration that without the coating, 220 or 230, the porous material 210 will allow liquid flow.

Thus, it is seen that an apparatus and method for demonstrating or testing the liquid, vapor and/or gas permeability characteristics of a surface coating are provided. One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well.

What is claimed is:

1. A gas permeability demonstration or testing apparatus comprising a test block including:

a substrate material that is permeable to a liquid;

a first coating material coated on at least a portion of the substrate material, wherein the coating material is substantially impermeable to liquid, but is relatively permeable to a gas;

a pressurized gas source in communication with the test block;

a liquid vessel in communication with the test block, but nor with the pressurized gas source;

whereby a pressure gradient is created between the pressurized gas source and the liquid vessel across the test block.

2. The apparatus of claim 1 wherein the pressure source includes a pressure chamber defining an interior space wherein the test block is in communication with the interior space of the pressure chamber.

3. The apparatus of claim 2 wherein the pressure source further includes:
   an input port providing access to the interior space of the pressure chamber from the exterior,
   a pressure line including first and second ends, the first end of the line connected to the input port; and
   a pump connected to the second end of the line.

4. The apparatus of claim 2 wherein the pressure chamber includes a first wall defining an aperture, wherein the test block is mounted on the first wall, covering the entire aperture.

5. The apparatus of claim 4 wherein the test block is connected to the first wall in a sealed fashion using a sealing medium.

6. The apparatus of claim 5 wherein the sealing medium comprises caulking.

7. The apparatus of claim 1 wherein the liquid vessel contains water.

8. The apparatus of claim 1 wherein the liquid vessel includes a bottom surface defining an aperture corresponding to the aperture in the first wall of the pressure chamber.

9. The test block of claim 1 wherein the liquid is water and the gas is air.

10. The test block of claim 1 further comprising a second coating material coated on at a portion of the substrate material, the second coating being substantially impermeable to the fluid and relatively permeable to the gas.

11. The test block of claim 10 wherein the first coating material coats the entire substrate material and the second coating material is coated on one surface thereof.

12. A method for demonstrating the liquid and vapor or gas permeability characteristics of a coating material in an apparatus including a test block having a porous base material at least partially coated with a test coating, a pressure source, and a liquid vessel comprising:
   placing a liquid in the liquid vessel;
   creating a pressure gradient across said test block from said pressure source, through the test block to the liquid vessel; and
   observing whether any gas or vapor has passed through said test block.

13. The method of claim 12 wherein said observing step includes visually observing whether any bubbles have passed through said liquid in said liquid vessel, the bubbles emanating from a portion of the test block exposed to said liquid in said liquid vessel.

14. The method of claim 12 wherein said pressure source includes a pressure chamber defining an interior space wherein the test block is exposed to the interior space of the chamber and the step of creating a pressure gradient across said test block includes raising the pressure in the interior space of the pressure chamber to a level above the pressure in the liquid vessel.

15. The method of claim 14 wherein said step of creating a pressure gradient further comprises pumping air into the pressure chamber.

16. The method of claim 15 wherein the step of pumping air comprises squeezing a rubber ball connected to the interior of the pressure chamber via a hose.

* * * * *